United States Patent [19]

Simón et al.

[11] Patent Number: 4,515,767

[45] Date of Patent: May 7, 1985

[54] RADIOACTIVE METALS COMPLEXED WITH PHOSPHONATE DERIVATIVES OF DICYCLOPENTADIENEBIS(METHYLAMINE)

[75] Inventors: Jaime Simón, Angleton; David A. Wilson, Richwood, both of Tex.; Wynn A. Volkert, Columbia, Mo.

[73] Assignee: The Dow Chemical Company, Midland, Mich.

[21] Appl. No.: 505,665

[22] Filed: Jun. 20, 1983

[51] Int. Cl.³ .................... A61K 49/00; A61K 43/00
[52] U.S. Cl. .................... 424/1.1; 260/429 J; 260/429.2; 260/429.7; 260/502.5 E; 562/499; 424/9
[58] Field of Search ............... 260/429 J, 429.2, 429.7, 260/502.5 E; 424/1.1, 9; 562/499

[56] References Cited

U.S. PATENT DOCUMENTS

| | | | |
|---|---|---|---|
| 3,851,044 | 11/1974 | Adler et al. | 423/249 |
| 3,852,414 | 12/1974 | Adler et al. | 424/1 |
| 3,931,396 | 1/1976 | Bardy et al. | 424/1 |
| 3,983,227 | 9/1976 | Tofe et al. | 424/1 |
| 3,989,730 | 11/1976 | Subramanian et al. | 260/429.7 |
| 4,016,249 | 4/1977 | Adler et al. | 424/1 |
| 4,023,625 | 6/1977 | Subramanian et al. | 424/1 |
| 4,075,314 | 2/1978 | Wolfangel et al. | 424/1 |
| 4,082,840 | 4/1978 | Adler et al. | 424/1 |
| 4,387,087 | 6/1983 | Deutsch et al. | 424/1.1 |

OTHER PUBLICATIONS

Radiology, vol. 99, pp. 192–196, 1971.
Radiology, 136: 209–211, Jul. 1980.
Radiology, 136: pp. 747–751, Sep. 1980.
J. Nuc. Med. 21: pp. 767–770, 961–966, (1980).

*Primary Examiner*—Christine M. Nucker
*Attorney, Agent, or Firm*—A. C. Ancona

[57] ABSTRACT

Complexes of radionuclides with a compound of the formula

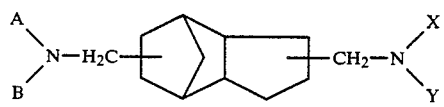

wherein substituents A, B, X and Y are each independently selected from radicals including hydrogen, hydroxyalkyl (wherein the alkyl group contains 2–6 carbon atoms) phosphonic, sulfonic, methylenephosphonic, methylene-, ethylene- and propylene-sulfonic, carboxylic acid radicals (having 2–4 carbon atoms) and the alkali or alkaline earth metal, ammonia and amine salts, thereof and wherein at least one A, B, X and Y is methylenephosphonic acid or a salt thereof. Tc-99m complexes have been found useful for imaging the skeletal structure of animals.

20 Claims, No Drawings

RADIOACTIVE METALS COMPLEXED WITH PHOSPHONATE DERIVATIVES OF DICYCLOPENTADIENEBIS(METHYLAMINE)

BACKGROUND OF THE INVENTION

The first radionuclide to be widely used for bone scanning was Sr-85. Strontium-85 is rapidly accumulated by bone after intravenous administration and images of the skeletal system are possible. However, Sr-85 has a long physical half life (65 days) and a long biological half life (~800 days) which limits the levels which can be administered. Also, the high energy of the gamma photon emitted (514 kev) is difficult to collimate.

Fluorine-18 has also been used to image the skeletal system. It is a positron emitter with a half life of 1.85 hr. Although F-18 has good physical properties for imaging, it has some serious drawbacks. Fluorine-18 is cyclotron produced and, therefore, expensive. Also its distribution is limited due to its short half life.

Many organ scanning agents, including those for the skeletal system, have now been replaced with complexes of Technetium-99 m. This nuclide has ideal physical properties ($T_{\frac{1}{2}}$=6 hr., gamma photon of 141 kev) for imaging. In addition, it is readily available because of the Mo-99/Tc-99 m generators. Thus, the majority of imaging is now done using Tc-99 m.

Technetium-99 m is obtained from generators in the +7 oxidation state as the pertechnetate ion ($TcO_4^-$). In order to form a complex, Tc must be in a lower oxidation state, i.e. +3, +4 or +5. Although other reducing agents can be used, $Sn^{2+}$ has been employed most often. Thus Tc-99 m complexes can be formed by reduction of $TcO_4^-$ using $Sn^{2+}$ in the presence of a complexing agent. This is usually done in an aqueous saline solution that is suitable for intravenous injection.

Commercial complexing agents are sold as "radiopharmaceutical kits". A "kit" consists of an evacuated vial containing the complexing agent, a reducing agent, and possibly a buffer and stabilizers. To prepare the Tc-99 m complexes, a few milliliters of sodium pertechnetate solution in saline is injected into the vial. An adequate amount of the resultant solution is used for imaging.

Subramanian et al (Radiology, Vol. 99, pp. 192-196, 1971 reported the use of a complex of Tc-99 m and an inorganic polyphosphate for skeletal imaging. Several others have reported inorganic polyphosphates as useful for this purpose (see U.S. Pat. Nos. 3,852,414; 4,016,249; and 4,082,840). The use of pyrophosphate (PYP) for bone imaging has also been taught (U.S. Pat. Nos. 3,851,044; 3,931,396; and 4,075,314). The Tc-phosphates had fair success but have been replaced by Tc-phosphonates.

Complexes of Tc-99 m with phosphonic acids show higher bone uptake with faster blood clearance than Tc-99 m/phosphate complexes. Phosphonic acids which are considered the best bone scanning agents when complexed with Tc-99 m include hydroxyethanediphosphonate (EHDP), methylenediphosphonate (MDP) and hydroxymethylenediphosphonate (see U.S. Pat. Nos. 3,983,227; 3,989,730; 4,032,625 and also J. Nucl. Med. 21, pg. 767; Radiology 136, pg. 209; J. Nucl. Med. 21, pg. 961; Radiology 136, pg. 747).

Evaluation of skeletal imaging agents has been, for the most part, limited to comparing total bone uptake to the rate of blood clearance through the kidneys in order to arrive at the best contrast between bone and soft tissue. However, it has been suggested that better lesion detection may be possible if the scanning agents have a high uptake in fast growing bone as compared with normal bone (see Clinical Nuclear Medicine, Vol. 7, pg. 403). Therefore a need exists for a Tc-99 m complex with high ratios of fast growing bone/normal bone uptake.

Another application for agents that have high ratios of fast growing bone to normal bone uptake is as a therapeutic agent. It may be possible to treat bone metastasis with a beta emitting radionuclide if it can be concentrated in the area of the metastasis. Therefore, if a beta-emitting agent that had a high uptake in fast growing bone and relatively low uptake in normal bone was found, it could prove to be an effective therapeutic agent.

Several nuclides may be of therapeutic utility. For example Re-186 has a half life of 90.6 hr. and beta-radiation of 1.076 and 0.939 MeV. Also, since the chemistry of Re is very similar to that of Tc, it is probable that the biolocalization of Re-complexes would be similar to that of Tc-complexes. There are other nuclides, especially of the lanthanide group of metals, that may also be therapeutically useful.

SUMMARY OF THE INVENTION

New stable complexing agents for Tc-99 m and Re-186 which are methylenephosphonate derivatives of dicyclopentadienebis(methylamine) have been found which are useful in imaging the skeletal system in animals. The complexes readily clear through the kidneys with large amounts being taken up in the bone. The ratio of uptake in fast growing bone to that in normal bone is high.

DETAILED DESCRIPTION OF THE INVENTION

This invention concerns the use of novel complexes for imaging the skeletal system and for possible treatment of skeletal metastasis. The complexing agents were found to form stable Tc-99 m complexes when $Sn^{2+}$ was added to a saline solution containing the complexing agent. The complex clears readily through the kidneys with a large amount being taken up by the skeletal system.

It was also discovered that the ratio of activity in fast growing bone to normal bone is higher than for complexes prepared with commercial diphosphonate kits. Therefore, it may be possible to visualize and more clearly distinguish bone lesions with the complexes of this invention. It may also be possible to treat skeletal metastasis with analogous complexes of a beta-emitting nuclide, e.g. Re-186.

The complexing agents useful in this invention, which are derivatives of 3(4),8(9)-bis(aminomethyl)-tricyclo[5.2.1.0$^{2,6}$]decane, also called dicyclopentadiene-bis(methylamine), are disclosed as new compounds in copending application entitled "New Metal Ion Control Agents Based on Dicyclopentadiene Derivatives", Ser. No. 486,122 filed Apr. 18, 1983.

The structure of the complexing agents has the following formula

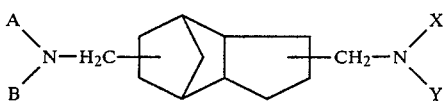

wherein substituents A, B, X and Y are each independently selected from radicals including hydrogen, hydroxyalkyl (wherein the alkyl group contains 2–6 carbon atoms) phosphonic, sulfonic, methylenephosphonic, methylene-, ethylene- and propylene-sulfonic, carboxylic acid radicals (having 2–4 carbon atoms) and the alkali or alkaline earth metal, ammonia and amine salts, thereof and wherein at leat one A, B, X and Y is methylenephosphonic acid or a salt thereof.

EXAMPLE 1

Deionized water (100 g) and 49.0 g (0.25 mole) of 3(4),8(9)-bis(aminomethyl)-tricyclo[5.2.1.0$^{2,6}$]decane also named 5(6)-(aminomethyl)-octahydro-4,7-methanoindene-1(2)-ylmethylamine) were weighed into a 500-ml round-bottom reaction flask equipped with a water-cooled reflux condenser, mechanical stirrer, thermometer, with a temperature controller, and an addition funnel. Approximately 120 g of concentrated HCl solution and 98.7 g (1.20 mole) of phosphorous acid were added to the aqueous amine solution and the reaction mixture heated to reflux and maintained for one hour. Aqueous 37% formaldehyde solution (85.1 g, 1.05 mole) was added to the addition funnel and added over a two-hour period. The reaction mixture was heated at reflux for an additional two hours and then cooled.

Two hundred microliters of the above solution were mixed with one ml of 0.9% NaCl solution and bubbled with $N_2$. The pH was adjusted to 3 using dilute NaOH and HCl and 0.1 ml of freshly eluted NaTcO$_4$ solution from a generator was added. To this solution, 100 μl of freshly prepared stannous tartrate (SnC$_4$H$_4$O$_6$) was added. Paper chromatography using saline and acetone as eluents showed less than 5% of the activity as TcO$_4^-$ or reduced uncomplexed Tc.

Fifty μl of the complex prepared above was injected into a laboratory rat. Scintillation scans done at intervals during a two-hour post injection period showed skeletal images of diagnostic quality.

EXAMPLE 2

Fifty μl of the complex prepared in Example 1 was injected into unanesthetized mice through the tail vein. They were killed at 15, 30 and 60 minutes post injection and their tissues removed and the radiation measured, using a NaI counter. The results, shown in Table 1, indicate a high percentage of the absorption in the bone, and relatively low absorption in other tissue. This data is consistent with that of Example 1 where good bone scans were observed in rats.

TABLE I

| Time (min.) Post Injection | % Dose/gram | | |
|---|---|---|---|
| | Bone | Muscle | Liver |
| 15 | 3.9 | 0.31 | 1.2 |
| 30 | 3.0 | 0.10 | 0.68 |
| 60 | 6.4 | 0.10 | 0.77 |

EXAMPLE 3

Fifty μl of the complex prepared in Example 1 was injected into the vein of anesthetized laboratory rats. After 120 minutes the animals were killed and the femurs removed. The ends of the bones were cut away from the mid-section and each section was weighed and analyzed separately. The amount of activity in the bone sections was quantitated using NaI scintillation counting. The results were compared to those of complexes prepared from commercial diphosphonate kits (Table II).

TABLE II

| | % Dose/gram | | |
|---|---|---|---|
| | End Bone | Midbone | End-/Mid-bone |
| PYP | 3.50 | 1.78 | 1.97 |
| MDP | 3.95 | 1.90 | 2.08 |
| EHDP | 3.40 | 1.46 | 2.33 |
| Complex of Example 1 | 3.60 | 1.42 | 2.54 |

We claim:

1. A bone seeking complex of a radioactive nuclide and a compound having the structural formula

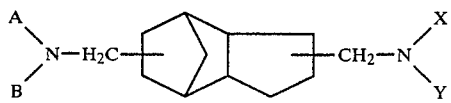

wherein substituents A, B, X and Y are each independently selected from radicals including hydrogen, hydroxyalkyl (wherein the alkyl group contains 2–6 carbon atoms) methylenephosphonic, methylene-, ethylene- and propylene-sulfonic, carboxylic acid radicals (having 2–4 carbon atoms) and the alkali or alkaline earth metal, ammonia and amine salts, thereof and wherein at least one A, B, X and Y is methylenephosphonic acid or a salt thereof.

2. The complex of claim 1 wherein A, B, X and Y are each methylenephosphonic acid radicals or salts thereof.

3. The complex of claim 1 wherein the radioactive nuclide is Technetium-99 m.

4. The complex of claim 2 wherein the radioactive nuclide is Technetium-99 m.

5. A composition comprising the complex of claim 3 and a reducing agent in a saline solution.

6. A composition comprising the complex of claim 4 and a reducing agent in a saline solution.

7. The composition of claim 5 wherein the reducing agent is $Sn^{2+}$.

8. The composition of claim 6 wherein the reducing agent is $Sn^{2+}$.

9. The composition of claim 1 wherein the radioactive nuclide is a beta or alpha emitter.

10. The composition of claim 2 wherein the radioactive nuclide is a beta or alpha emitter.

11. The composition of claim 9 wherein the radionuclide is Re-186.

12. The composition of claim 10 wherein the radionuclide is Re-186.

13. A composition comprising the complex of claim 11 and a reducing agent in a saline solution.

14. A composition comprising the complex of claim 12 and a reducing agent in a saline solution.

15. The composition of claim 13 wherein $Sn^{2+}$ is the reducing agent.

16. The composition of claim 14 wherein $Sn^{2+}$ is the reducing agent.

17. The composition of claim 9 wherein the radionuclide is one of the lanthanide series of the periodic table.

18. The composition of claim 10 wherein the radionuclide is one of the lanthanide series of the periodic table.

19. In a process in which the skeletal system is imaged with a complex of a radionuclide the improvement which comprises employing as the complexing agent a compound having the formula

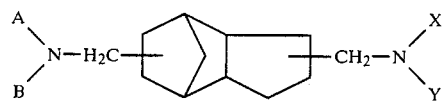

wherein substituents A, B, X and Y are each independently selected from radicals including hydrogen, hydroxyalkyl (wherein the alkyl group contains 2–6 carbon atoms) methylenephosphonic, methylene-, ethylene- and propylene-sulfonic, carboxylic acid radicals (having 2–4 carbon atoms) and the alkali or alkaline earth metal, ammonia and amine salts, thereof and wherein at least one A, B, X and Y is methylenephosphonic acid or a salt thereof.

20. The process of claim 19 wherein A, B, X and Y are each a methylenephosphonic acid or a salt thereof.

* * * * *